United States Patent [19]

Small

[11] 4,439,152

[45] Mar. 27, 1984

[54] METHOD OF JAWBONE ABUTMENT IMPLANT FOR DENTAL PROSTHESES AND IMPLANT DEVICE

[76] Inventor: Irwin A. Small, 6861 Orinoco Cir., Birmingham, Mich. 48010

[21] Appl. No.: 354,789

[22] Filed: Mar. 4, 1982

[51] Int. Cl.³ .............................................. A61C 8/00
[52] U.S. Cl. .................................. 433/173; 433/174; 128/92 C
[58] Field of Search ............... 433/173, 174, 175, 176, 433/201, 220, 221; 3/1.9, 1.91, 1.911, 1.912, 1.913; 128/92 C

[56] References Cited

U.S. PATENT DOCUMENTS

| | | | |
|---|---|---|---|
| 3,499,222 | 3/1970 | Linkow et al. | 433/174 |
| 3,589,011 | 6/1971 | Sneer | 433/174 |
| 3,683,501 | 8/1972 | Edelman | 433/176 |
| 3,745,590 | 7/1973 | Stubstad | 3/1.9 |
| 3,826,241 | 7/1974 | Bucalo | 433/173 |
| 3,849,887 | 11/1974 | Brainin | 433/201 |
| 3,863,344 | 2/1975 | Pillet | 433/173 |
| 3,906,550 | 9/1975 | Rostoker et al. | 433/201 |
| 3,934,347 | 1/1976 | Lash et al. | 128/92 C |
| 3,952,414 | 4/1976 | Shovers et al. | 433/173 |
| 3,979,828 | 9/1976 | Taylor | 433/175 |
| 4,064,567 | 12/1977 | Burstein et al. | 3/1.91 |
| 4,089,071 | 5/1978 | Kalnberz et al. | 3/1.9 |
| 4,252,525 | 2/1981 | Child | 433/173 |
| 4,253,833 | 3/1981 | Edelman | 433/173 |
| 4,261,063 | 4/1981 | Blanquaert | 3/1.91 |
| 4,379,694 | 4/1983 | Riess | 433/173 |

*Primary Examiner*—John J. Wilson
*Attorney, Agent, or Firm*—Cullen, Sloman, Cantor, Grauer, Scott & Rutherford

[57] ABSTRACT

The method of implanting an abutment device to a jawbone for anchoring a dental prosthesis comprises surgically cutting gum tissue, turning back adjacent tissue exposing the jawbone, drilling into the bone, assembling a hollow porous cylinder of titanium wire mesh having threaded therein a temporary nylon plug into the jawbone, reassembling the gum tissue to overlie the cylinder and plug. Retaining the cylinder for a healing period of several months while adjacent bone tissue grows into, around and through the cylinder mesh for a mechanical interlock therewith for anchoring the cylinder with the jawbone. Surgically reexposing the cylinder, removing the plug from the cylinder and successively threading therein an abutment device, an axial portion thereof projecting from the jawbone and gum tissue to which a dental prosthesis may be attached. A jawbone implant comprises a hollow porous cylinder of titanium wire mesh having a threaded bore with a nylon plug threaded therein for projecting into an aperture in a jawbone. After a healing period while bone tissue migrates into and through the mesh for a mechanical interlock, an abutment device replaces the plug and has an axial portion projecting from the jawbone to which a dental prosthesis is attached. A modified method after exposing the jawbone includes applying to the exposed bone a pair of spaced cylinders of wire mesh with an interconnecting strip of similar mesh, the cylinders having a temporary nylon plug threaded thereinto, and applying a strip of open mesh plastic or titanium wire to the cylinders, assembling and clamping portions of the open mesh strip to surround the cylinders retaining the cylinders and interconnected mesh strip of material upon the bone. Successively exposing the cylinders, unthreading the plugs and threading into each cylinder an abutment, to which a dental prosthesis may be attached. A jawbone implant device therefore.

22 Claims, 13 Drawing Figures

METHOD OF JAWBONE ABUTMENT IMPLANT FOR DENTAL PROSTHESES AND IMPLANT DEVICE

BACKGROUND OF THE INVENTION

Heretofore, and particularly with older people including senior citizens, difficulty has been experienced in retaining and anchoring a dental or orthopedic prosthesis upon the jaws, including the mandible or lower jaw and the maxilla or upper jaw due to wasting away of gum tissue. Various efforts have heretofore been made for providing some form of mechanical anchoring device which extends through or into the corresponding jawbone and includes projections adapted to interlockingly position within corresponding apertures within the dental or orthopedic prosthesis for anchoring same against movements with respect to the jawbone and particularly transverse movements.

Recognition of and a means for solving the problem are disclosed in Applicant's U.S. Pat. No. 3,414,975 of Dec. 10, 1968 to and U.S. Pat. No. 3,664,022 dated May 23, 1972 both directed to a Drill Guide for Mandibular Staples and Staple Construction. One of the difficulties with the use of a Mandibular Staple was the necessity for surgically exposing the jaw bone outside the chin and carefully and accurately drilling apertures through the mandible, and thereafter projecting the U-shaped staple therethrough and securing the staple in place.

The Staple disclosed in said patents was not normally used for or particularly adaptable to the upper jaw or maxilla.

Heretofore in the prior art, various efforts have been made for the anchoring of devices into the upper or lower jawbone including projections away from the jawbone adapted for interlock with corresponding apertures within a dental or orthopedic prosthesis.

THE PRIOR ART

Illustration of said prior art efforts are shown in one or more of the following U.S. patents and hereunder identified publications:

U.S. Pat. No. 3,852,045 to Kenneth R. Wheeler, Dec. 3, 1974;

U.S. Pat. No. 3,919,772 to Joseph J. Lenczycki, Nov. 18, 1975;

U.S. Pat. No. 3,919,773 to Frank Hubert Freeman, Nov. 18, 1975;

U.S. Pat. No. 3,934,347 to Harvey Lash, Jan. 27, 1976;

U.S. Pat. No. 3,952,414 to Aaron H. Shovers, Apr. 27, 1976;

U.S. Pat. No. 3,992,780 to Imre Herskovits, Nov. 23, 1976;

U.S. Pat. No. 4,011,602 to Edmund F. Rybicki, Mar. 15, 1977;

U.S. Pat. No. 4,064,567 to Albert H. Burstein, Dec. 27, 1977;

U.S. Pat. No. 4,065,817 to Per Ingvar Branemark, Jan. 3, 1978;

U.S. Pat. No. 4,180,910 to Fritz Straumann, Jan. 1, 1980;

U.S. Pat. No. 4,222,128 to Atsushi Tomonaga, Sept. 16, 1980;

U.S. Pat. No. 4,252,525 to Frank W. Child, Feb. 24, 1981;

U.S. Pat. No. 4,259,072 to Masaya Hirabayashi, Mar. 31, 1981.

RECONSTRUCTION OF ALVEOLAR JAWBONE, an experimental and clinical study of immediate and preformed autologous bone grafts in combination with Osseointegrated Implants.

Scand J Plast Reconstruction Surgery 14:23–48, 1980, pages 23 through 48.

Investigation of Long-Term Performance of Porous-Metal Dental Anchors in Nonhuman Primates.

Battelle Pacific Northwest Laboratories, August, 1981, pages 1 through 29.

SUMMARY OF THE INVENTION

The present invention relates to the use of meshed titanium wire cylinders to function as bone fastening devices for orthopedic, oral and maxillofacial surgery in cases where implantable devices require fixation to bone, such as the mandible and maxilla, lower and upper jaw structures. The titanium wire mesh is an open pore construction which will allow bone to grow in and around and through the wire framework for firm anchoring of the device.

The titanium mesh is formed as a hollow cylinder with internal threading for insertion of a temporary nylon plug. The Nylon or Teflon plug and titanium wire mesh cylinder are completely buried in the jaw bone until healing and fixation are complete.

The buried cylinders are then surgically reexposed, the nylon plug removed and replaced with an abutment post or retaining device to which a dental prosthesis or orthopedic prosthesis can be attached.

The present invention is directed to a method of implanting a bone fastening device within a jawbone wherein after location of the implantation area, mucosa or gum tissue is surgically cut and turned back exposing the jawbone, after which a hole is drilled thereinto. A porous cylinder of titanium wire mesh with temporary threaded plug therein is inserted within the jawbone and the severed gum tissue is reassembled to bridge the cylinder. The cylinder and plug are retained for a healing period of several months while adjacent bone tissue migrates and grows into, around and through the cylinder wire framework for a mechanical interlock therewith for firmly anchoring and fixing the cylinder within the jawbone. Additional steps include the cutting of the gum tissue and surgically reexposing cylinder and plug to permit unthreading and removing of the plug from the cylinder. A replacement abutment retaining device of titanium is successively threaded into the cylinder and includes an axial portion which projects from the jawbone and gum tissue to which a dental or orthopedic prosthesis may be attached.

A further feature of the present invention includes a jawbone implant for orthopedic, oral or maxillofacial surgery which comprises hollow porous cylinder of titanium wire mesh having a threaded bore adapted for projection into an aperture in the jawbone and having threaded thereinto a temporary plug of nylon. The cylinder and plug adapted to be retained within the jawbone for a healing period of several months and thereafter an abutment device of titanium replaces the plug within the cylinder. An axial portion of the abutment projects from the jawbone and gum to which a dental or orthopedic prothesis may be attached.

A further feature includes a modified method utilizing flexible subperiosteal retaining cylinders and abutments wherein the titanium wire mesh cylinders are attached to a thin plastic mesh or titanium wire mesh strip which is embedded under the periosteal layer at the bone which then acts as a means of anchoring and retaining the device for a prosthesis.

The open mesh work plastic fabric or wire mesh strip is placed under the dense periosteum of bone and the open mesh system allows the periosteum to reattach to the bone and thus anchor the device firmly thereto.

A further feature includes flexibility of the use of plastic or wire mesh stripping which allows draping and fitting the device upon various anatomical shapes and countours of bone. The plastic or wire mesh strip is placed under the periosteal layer adjacent the bone with portions thereof distant from the site of the abutments and thereby provides a stronger anchoring therefor.

A pair of titanium wire mesh cylinders, attached to eachother by a strip of titanium wire mesh are fastened to the plastic mesh strip by a snap on ring which fits over the titanium mesh cylinders and traps the plastic mesh strip upon the exterior of said cylinders surrounding said cylinders. The concave inner surface of the ring extends around the convex outer surface of the titanium cylinder.

The titanium cylinders have a central nylon plug which is threaded thereinto. The whole assembly is completely buried for several months under the periosteal layer until healing is complete. After healing, the tops of the cylinders are surgically reexposed, the nylon plugs removed and replaced with titanium abutments of either a male or female version and to which can be attached a medical or dental prosthesis.

A further feature is directed to the structure of a pair of spaced titanium wire mesh cylinders which are interconnected at their one ends by a strip of titanium wire mesh, wherein the cylinders are used in conjunction with a strip of open plastic mesh or titanium wire mesh which is implanted upon an exposed portion of the jawbone and wherein the strip of mesh material extends laterally and longitudinally of the pair of cylinders. Portions of the plastic or titanium wire mesh are cylindrically formed to surround the cylinders and are clamped thereto so that after a healing process, the wire mesh strip is anchored over a large area to the adjacent jawbone by the periosteum growing through the plastic mesh or the titanium wire mesh and the replacement titanium abutments are adapted to retainingly engage a dental of orthopedic prosthesis.

These and other features and objects will be seen from the following specification and claims in conjunction with the appended drawings which are illustrative of the method and construction of the present mesh titanium wire cylinders and the flexible superiosteal retaining cylinders and abutments.

It will be understood that the above drawing illustrates the steps of the present method and modified method and the jawbone implants for orthopedic oral and maxillofacial surgery and that other steps and structures are included within the scope of the claims hereafter set forth.

DETAILED DESCRIPTION OF THE METHOD OF IMPLANTING BONE FASTENING DEVICES

Referring to FIGS. 1 through 8, there is disclosed the method of implanting a bone fastening device which includes the use of two or more buried wire mesh cylinders with central retaining plugs and delayed abutment inserts which will be used as a bone anchor and a prosthetic retaining device for dentists, oral surgeons and orthopedic surgeons.

Figures 1, 3, 4, 5, 6:
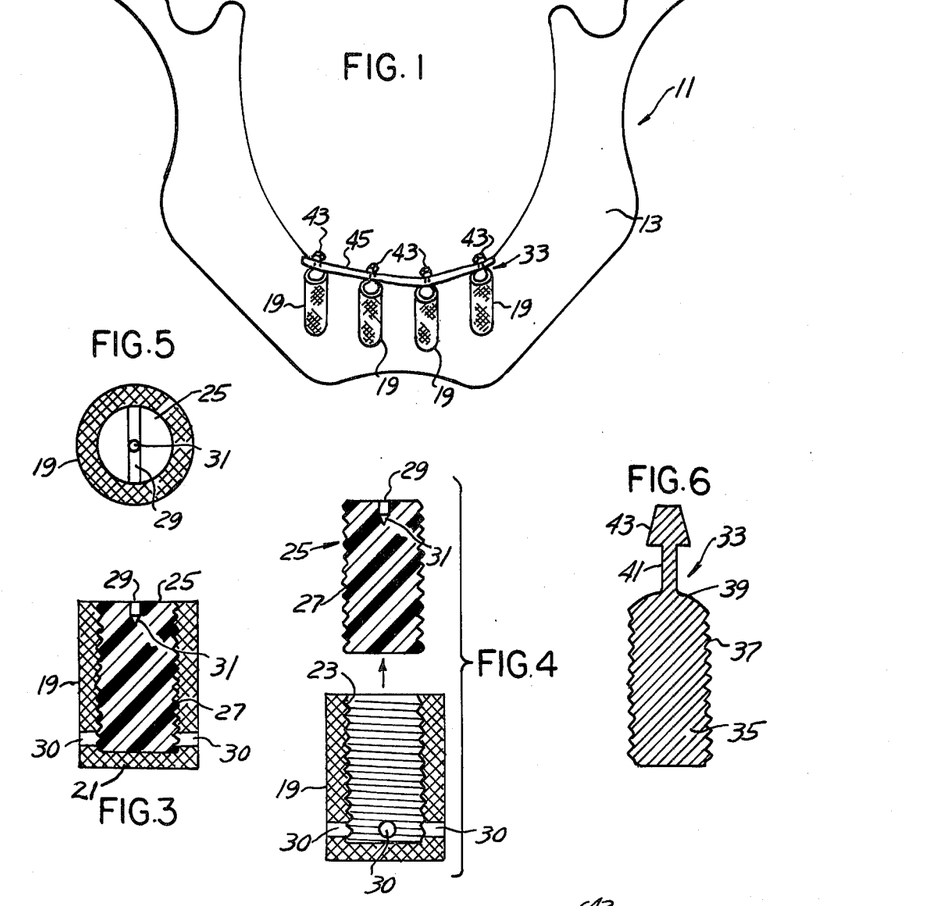
FIG. 1, is a schematic plan view of a human mandible within which a plurality of mesh titanium wire cylinders have been implanted, wherein titanium abutments project therefrom adapted for supporting interlock with dental or orthopedic prosthesis.
FIG. 3 is a vertical sectioned view of the titanium wire mesh cylinder and plug.
FIG. 4 is a similar view showing the threaded nylon plug removed from the cylinder as an exploded view.
FIG. 5 is a top plan view of the cylinder and assembled plug of FIG. 3.
FIG. 6 is a front view of the titanium abutment which replaces the nylon plug within the wire mesh cylinder.

A mandible or lower jaw is schematically shown at 11 in FIG. 1 including jawbone 13 sometimes referred to as alveolar bone, over which there is the conventional gum tissue including mucosa 15.

Figure 7:
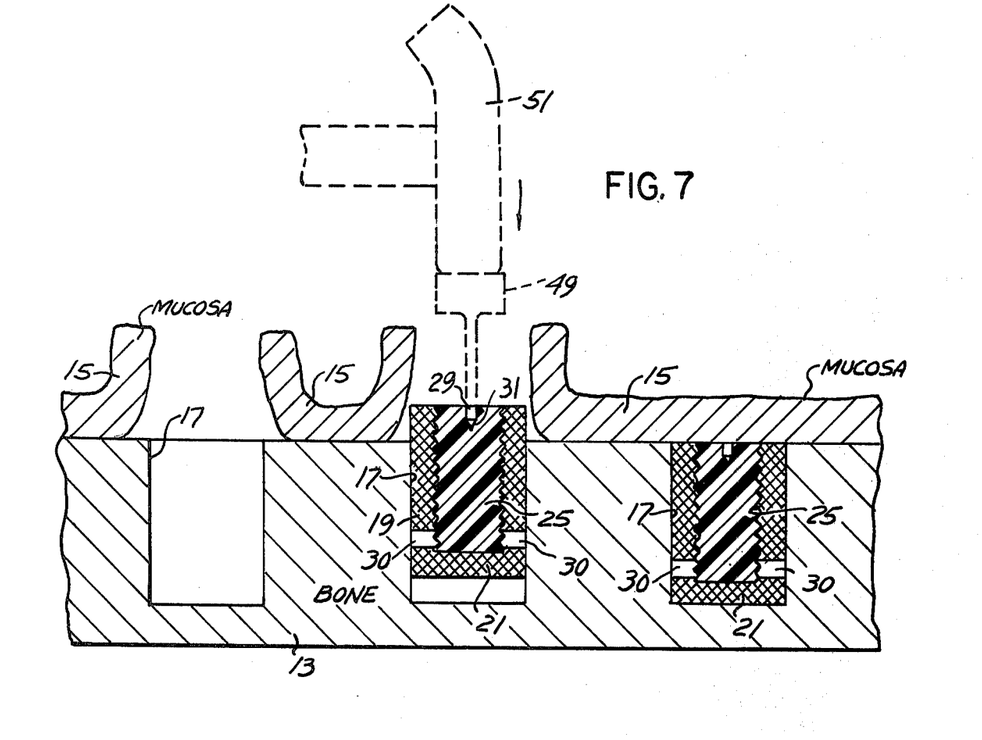
FIG. 7 is a schematic partially sectioned view illustrating some of the steps of the method of implanting the bone fastening device within a jawbone.
Figure 8:
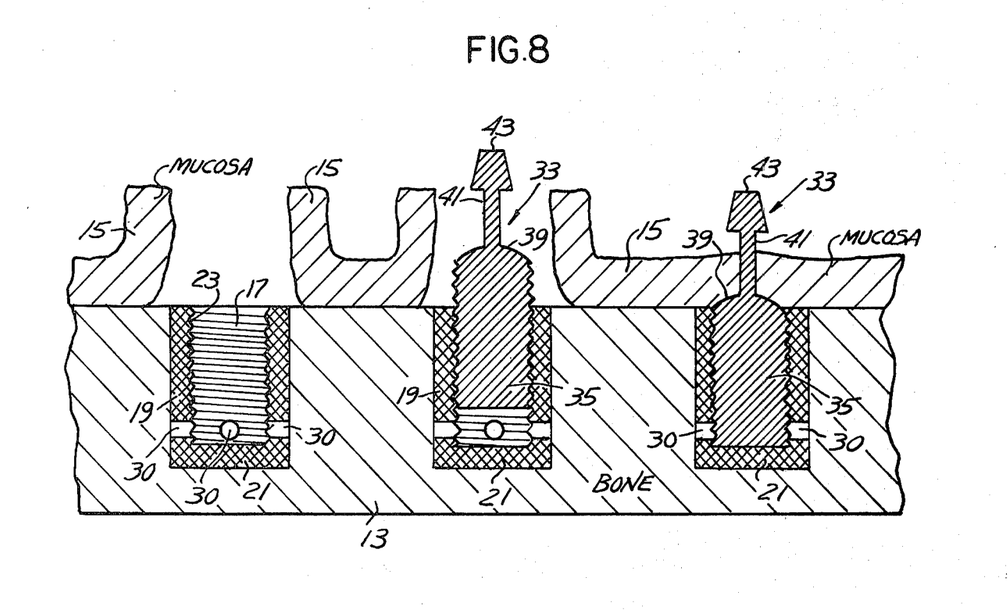
FIG. 8 is a similar view of additional steps forming a part of the method.

The method steps of the present invention are illustrated schematically in FIGS. 7 and 8 and include the location of the approximate areas for implantation of 2 or more bone fastening devices with respect to the mandible. The mucosa 15 is surgically cut, as shown on the left side of the illustration at the located area and the mucosa is turned back exposing the jawbone 13. The hole or bore 17 is drilled into the bone 13 to a predetermined depth and diameter.

A further step includes the selecting of a hollow porous cylinder 19 of titanium wire mesh, of a height and diameter corresponding to the hole depth and diameter.

For illustration, the cylinder has a height in the range of 10 to 20 m which corresponds to the depth of the hole 17, and has outside diameter of 10/64 inches corresponding to the diameter of the hole and has an interior threaded bore 23 which has a diameter of 6/64 inches, approximately.

Cylinder 19 has a transverse bottom wall 21 of titanium wire mesh. A plurality of spaced venting holes 30 extend through the cylinder above wall 21. These provide for ingrowth of plugs of bone for interlock therewith.

Figure 2:
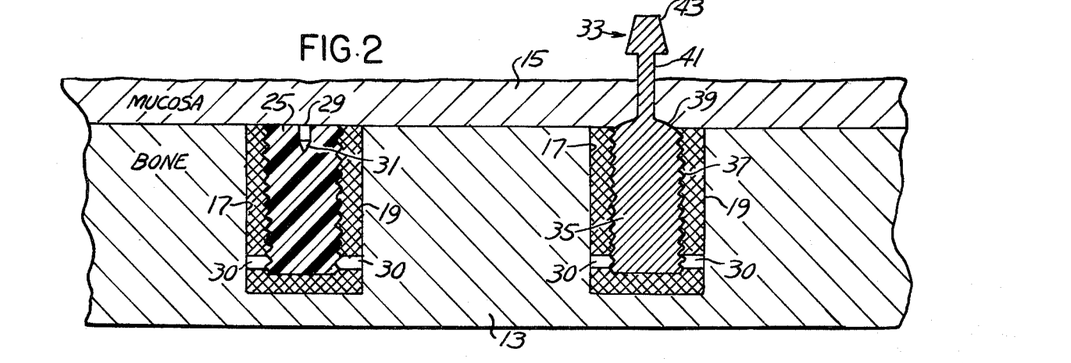
FIG. 2 is a fragmentary and schematic view illustrating the titanium abutment within a wire mesh cylinder implanted within a jawbone and projecting therefrom.

Plug 25 of Nylon or Teflon, exteriorly threaded at 27 has a transverse screwdriver slot 29 on the top thereof and a central bore 31, is adapted for threading into the cylinder 19 and enclosed thereby, FIGS. 2, 3 and 4. With the plug 25 threaded into the cylinder 19, the cylinder and plug are tapped down into the hole 17 using an impact tool 49 and mallet 51, FIG. 7, as shown in the center illustration.

As a further step the severed mucosa 15 is reassembled so as to snugly overlie and bridge the cylinder and plug, FIG. 7 right side.

Thereafter the cylinder and plug are retained within the jawbone for a predetermined healing period of several months, such as two to three months, while adjacent bone tissue 13 migrates and grows into, around and through the cylinder wire framework for a mechanical interlock therewith, firmly anchoring and fixing the cylinder within the jawbone. The temporary plug 25 closes the interior of the cylinder 19 and prevents migration of bone tissue into the interior thereof.

As a further step after the healing period, mucosa 15 again is surgically cut as shown on the left hand side of FIG. 8 and the adjacent tissue turned back. This is followed by unthreading and removing the plug 25. Successively as shown in the central illustration, there is threaded down into the cylinder 19 a replacement abutment retaining device 33 of titanium which in the final position has its body 35 which is threaded at 37 threaded down into the cylinder 19.

The body 35 at one end terminates in the neck 39 from which projects the axial portion 41 extending away from the jawbone 13 and terminates in the head 43 of irregular shape, such as square or polygonal and which is adapted for projection into a corresponding aperture of a dental or orthopedic prosthesis.

A further final step includes replacing the mucosa 15 as shown in the right hand illustration FIG. 8, so that portions thereof extend to the abutment 33 and overlie its neck 39 for sealing off the abutment assembly within the embedded cylinder 19.

In some situations there will be implanted within the mandible or within either jaw at least a pair of laterally spaced abutment retaining devices 33 whose respective heads 43 are adapted for interlocking projection within corresponding apertures in the undersurface of a bridge, a dental or orthopedic prosthesis.

The present invention also includes the structure of the jawbone implant and connected titanium abutment wherein there is included the above described hollow porous cylinder 19 of titanium wire mesh, FIG. 4 having an interior threaded bore 23 and threaded thereinto a temporary nylon plug 25. The assembled cylinder and plug are adapted to be retained within a hole 17, FIG. 7, drilled in the jawbone 13 for a predetermined healing period of two to three months while adjacent bone tissue migrates and grow into, around and through the cylinder wire framework for a mechanical interlock therewith. The present jaw implant also includes an abutment device 33 of titanium which is adapted to replace the plug 25, as shown in FIGS. 2 and 8.

In the illustration FIG. 1, there are four jawbone implants assembed and secured within the mandibular jawbone 13 for illustration, and wherein the respective heads 43 are interconnected by a transverse bar 45 wherein said heads and bar are adapted to be retainingly nested within corresponding apertures in the undersurface of a prosthetic device such as a bridge, anchoring the bridge upon the mandible and particularly for anchoring the bridge against transverse movements relative to the mandible or jaw.

MODIFIED METHOD OF IMPLANTING FASTENING DEVICE TO JAWBONE FLEXIBLE SUBPERIOSTEAL RETAINING CYLINDERS AND ABUTMENTS

Figure 9:
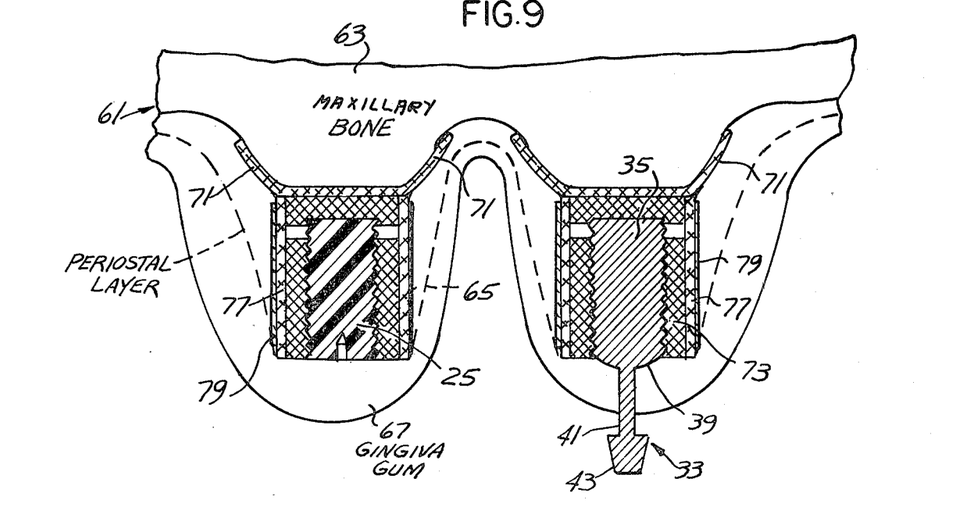
FIG. 9 is a fragmentary partly sectioned view of the human upper jaw bone with associated periosteal layer and gum tissue, within which there is shown a flexible subperiosteal retaining cylinder and abutment.

Referring to FIGS. 9 through 13, there is disclosed a method and apparatus which includes subperiosteal burried pair of cylinders 73 made of titanium wire mesh with assembled plugs 25 including a wire mesh connector 75 between the cylinders. Snap rings 79 holds the Nylon or Dacron or titanium wire mesh 71, which is placed upon and along the bone surface of the jaw under the periosteum. This device and the method may be used as a bone anchor and includes a similar feature namely, retaining the implant device for a period of healing of two to three months. Later the retaining plugs are exposed and removed and there is inserted abutments which will hold and stabilize a dental or orthopedic prosthesis. The present method is primarily directed to implanting a fastening device to the maxilla or upper jaw, though not limited thereto, as schematically shown in FIG. 9, the maxilla being shown at 61 as including the maxillary bone 63 sometimes referred to as the jawbone which has exteriorly thereof a periosteal layer 65 and outwardly thereof the gum tissue 67 sometimes referred to as gingiva.

Figure 10:
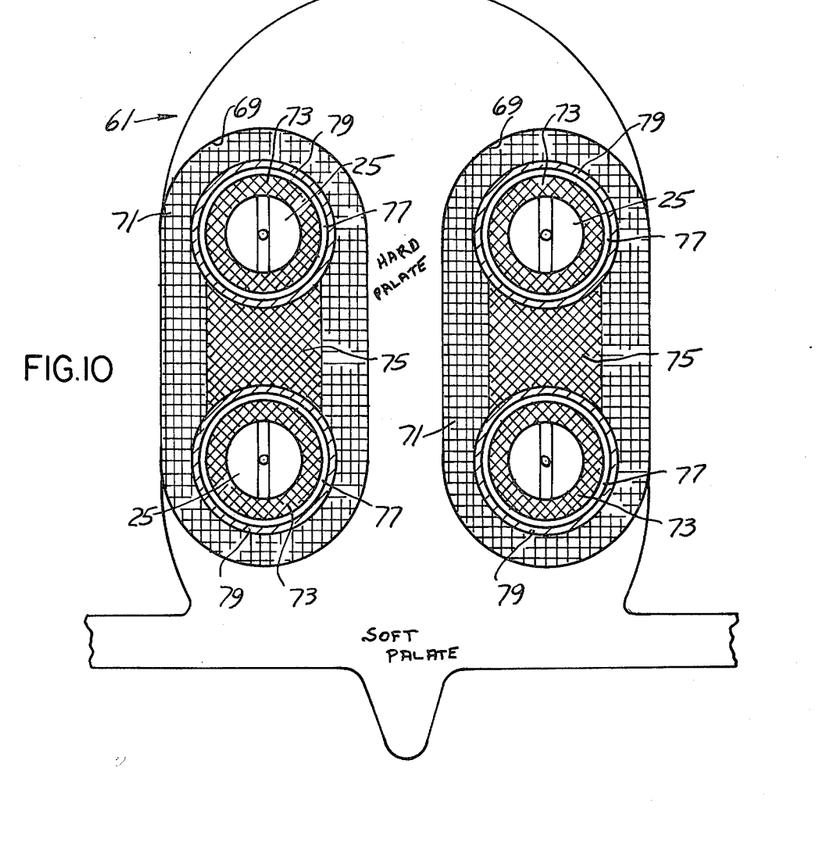
FIG. 10 is a bottom plan view of the upper jaw showing the opposed spaced pairs of flexible subperiosteal retaining cylinders and abutments implanted upon the upper jaw and retained thereon.
Figure 11:
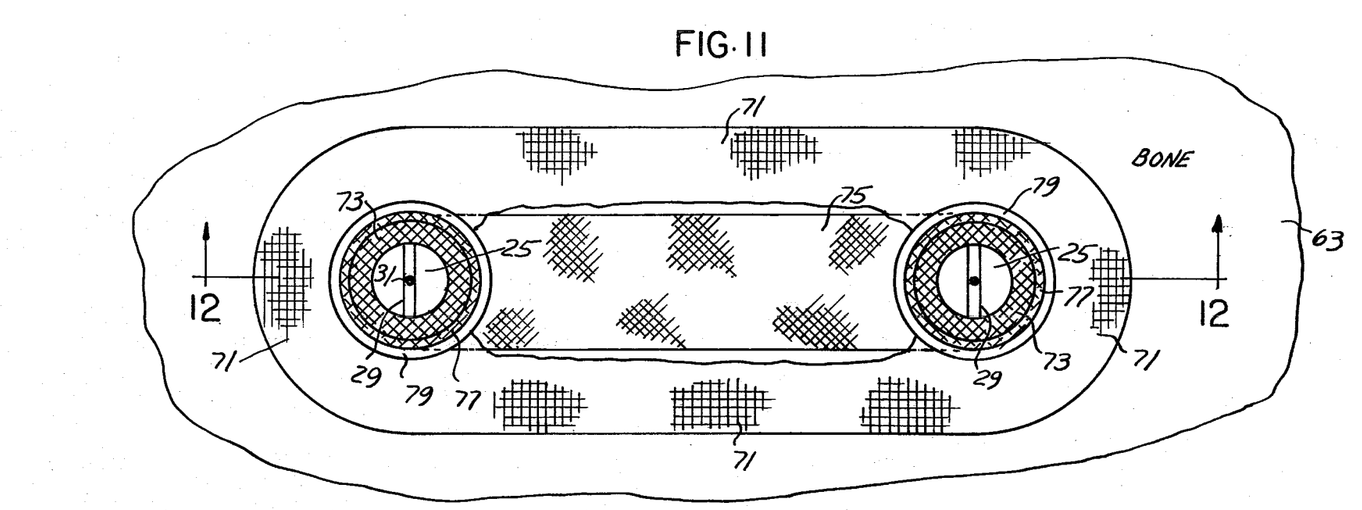
FIG. 11 is a plan view on an enlarged scale of one of the pairs of flexible subperiosteal retaining cylinders and abutments shown in FIG. 10.

The present modified method of implanting a fastening device upon the maxillary bone 63 includes the primary step of locating the approximate areas 69 for implantation such as shown in FIG. 10 and thereafter surgically cutting the gum tissue 67 and underlying periosteal layer 65 as at 69. Gum tissue and underlying periosteal layer 65 are turned back as in FIG. 7.

There is employed a pair of cylinders 73 of open titanium wire mesh which are spaced apart, FIG. 10, and are joined at their one ends by an elongated wire mesh connector 75 of titanium. This assembly is first applied to the exposed bone 63.

There is then applied over cylinders 73 and connector 75 a thin mesh strip of plastic or titanium wire at 71 which bears against the exposed maxillary bone 63. The plastic mesh strips 71 may be Dacron, or Teflon.

Figure 12:
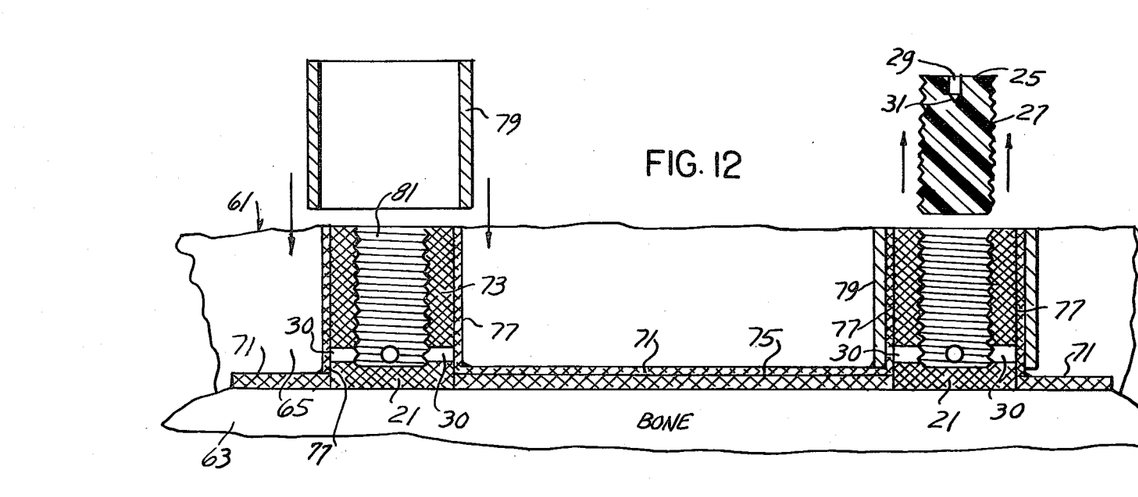
FIG. 12 is a fragmentary section thereof taken in the direction of arrows 12—12 of FIG. 11.
Figure 13:
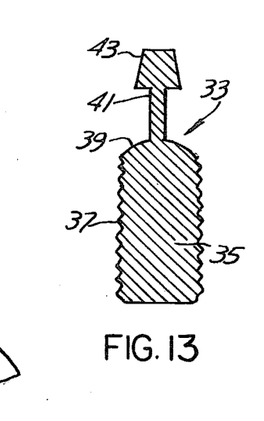
FIG. 13 is a front sectioned view of the abutment which replaces the nylon plug shown in FIG. 12.

The selected pair of hollow wire mesh cylinders 73, FIG. 12, are of a height which does not exceed the depth of the periosteal layer 65. A temporary nylon plug 25 is threaded into each of the wire mesh titanium cylinders 73

The cylinders and interconnected strip 75 centrally underlie the open mesh strip 71 and are in supported engagement with the bone surface 63, FIG. 9. As shown in FIG. 10, portions of the open mesh strip 71 extend laterally and longitudinally of the interconnected cylinders 73. Apertures are formed within the open mesh strip 71 at a center distance corresponding to the center distance between the cylinders 73, so as to receive said cylinders. The open mesh strip is formed into cylindrical portions 77 so as to surround the cylinders 73 and the said cylindrical portions forming a part of the mesh strip 71 are mechanically secured to adjacent areas of said cylinders enclosing them. In the illustrative embodiment the mechanical securing includes the snap on retaining ring 79 of a suitable plastic material which encloses the cylindrical formation 77 of the mesh strip and the wire mesh cylinders 71 retainingly and trapping portions of the open mesh strip 71 around said cylinders.

A further step includes the reassembling of the severed periosteal layer and gum tissue over the open mesh strip 71 and wherein the cylinders are embedded within the periosteal layer 65. Additionally the severed gum tissue is assembled so as to overlie and retainingly engage the cylinders and plugs as shown in the left hand illustration, in FIG. 9.

The interconnected cylinders 73 and their plugs 25 are retained for a predetermined healing period of two to three months within the periosteal layer which is a dense tissue layer while the adjacent periosteal layer reattaches to the bone in such manner as to flexibly anchor the open mesh strip 71 and the interconnected cylinders, to the bone in the manner shown in the left hand illustration, FIG. 9.

After that healing period, the gum tissue, which has been earlier marked so as to designate the areas of the cylinders, is again surgically cut to expose the cylinders, turning back the adjacent tissue in the manner shown in FIG. 8. The plugs 25 are unthreaded and removed from the cylinders 73 and successively threaded into each cylinder is a replacement abutment retaining device 33 of titanium.

As above described, the replacement abutment device includes body 35 exteriorly threaded at 37, having a neck 39 and shank 41 terminating in the polygonal head 43, which may be either male or female configuration.

The axial portion 41 of the abutment projects through and from the gum tissue 67 and outwardly thereof so that the heads 43 are adapted for projection into a corresponding spaced apertures within a dental or orthopedic prosthesis.

The method set forth with respect to FIGS. 9 through 13 includes the same cylinder construction 73 of an open mesh titanium wire above described in detail with respect to FIGS. 2 through 5 and additionally includes the titanium wire mesh strip 75 which interconnects the cylinders, FIG. 12 so that the assembly of the pair of connected cylinders and strip 75 is applied to the exposed bone 63 and thereover is applied the thin open mesh strip of Dacron, Teflon or titanium wire. Portions of the strip 71 are formed so as to cylindrically enclose and surround the interconnected cylinders as at 77 and are clamped thereon mechanically by the use of the snap rings 79.

Here the corresponding thin mesh strip of plastic or titanium wire is embedded, not into the bone, but upon the bone and under the periosteal layer 65 which when healed acts as an anchor and retaining device for a prosthesis.

The thin open mesh strip of plastic fabric or wire mesh 71 can be placed under the dense periosteum of bone as at 65 and the open mesh system will allow the periosteum to reattach to the bone and thus anchor the device firmly to the bone.

The flexibility of the plastic or wire mesh 71 will allow draping and fitting the device over various anatomical shapes and contours of bone such as shown in FIG. 9.

Since portions of the plastic or wire mesh strip 71 are placed under the periosteum 65 distant from the sight of the abutments 33, there is provided a stronger anchoring for the prosthetic device.

Having described my invention, reference should now be had to the following claims:

I claim:

1. The method of implanting a bone fastening device within a jawbone for orthopedic, oral and maxillofacial surgery which comprises the steps of:
   locating the approximate area for implantation;
   surgically cutting the mucosa at said area and turning back the adjacent tissue exposing the bone;
   drilling a hole into the bone of a predetermined depth and diameter;
   selecting a hollow porous cylinder of titanium wire mesh of appreciable wall thickness of a height and diameter corresponding to said hole depth and diameter;
   threading a temporary nylon plug into said cylinder;
   tapping the assembled cylinder and plug down into the filling said jawbone bone;
   reassembling the severed mucosa snugly overlying and bridging said cylinder and plug;
   retaining said cylinder and plug for a predetermined healing period of two to three months while adjacent bone tissue migrates and grows into, around and through the cylinder wire framework for a mechanical interlock therewith, firmly anchoring and fixing the cylinder within said jawbone;
   cutting the mucosa and surgically reexposing said cylinder and turning back the adjacent tissue;
   unthreading and removing said plug from said cylinder;
   and successively threading into said cylinder a replacement abutment retaining device of titanium;
   an axial portion thereof projecting from said jawbone and mucosa to which a dental or orthopedic prosthesis may be attached.

2. In the method defined in claim 1, the further step of reassembling the severed mucosa into snug engagement with projecting portions of said abutment and surrounding tissue.

3. In the method of claim 1, said cylinder being internally threaded.

4. In the method of claim 1, said nylon plug being exteriorly threaded and having in its top a transverse screw driver slot.

5. In the method of claim 1, said plug having a central aperture in its top adapted to receive an impact tool facilitating an axial thrust thereto for tapping into said jawbone.

6. In the method of claim 1, said replacement abutment including a threaded body nested in said cylinder, having a neck underlying said mucosa, and an axial shank extending from said neck through said mucosa and terminating in an abutment head laterally enlarged relative to said neck and spaced outwardly of said mucosa.

7. The method of implanting a pair of laterally spaced bone fastening devices within a jawbone upon opposite sides thereof for orthopedic, oral and maxillofacial surgery which comprises for each device the following steps:
   locating the approximate area for implantation;
   surgically cutting the mucosa at said area and turning back the adjacent tissue exposing the bone;
   drilling a hole into the bone of a predetermined depth and diameter;
   selecting a hollow porous cylinder of titanium wire mesh of a height and diameter corresponding to said hole depth and diameter;
   threading a temporary nylon plug into said cylinder;
   tapping the assembled cylinder and plug down into and filling said jawbone hole;

reassembling the severed mucosa snugly overlying and bridging said cylinder and plug;

retaining said cylinder and plug for a predetermined healing period of two to three months while adjacent bone tissue migrates and grows into, around and through the cylinder wire framework for a mechanical interlock therewith, firmly anchoring and fixing the cylinder within said jawbone;

cutting the mucosa and surgically reexposing said cylinder and turning back the adjacent tissue;

unthreading and removing said plug from said cylinder;

and successively threading into said cylinder a replacement abutment retaining device of titanium;

an axial portion thereof projecting from said jawbone and mucosa to which a dental or orthopedic prosthesis may be attached.

8. In the method of claim 7, the additional step of interconnecting the abutments of said pair of bone fastening devices with a bridge;

said abutments and bridge adapted for nesting within corresponding apertures in the undersurface of a dental or orthopedic prosthesis.

9. The method of implanting a fastening device upon a jawbone having a periosteal layer and overlying gum tissue for orthopedic, oral and maxillofacial surgery which comprises the following steps;

locating an approximate area for implantation;

surgically cutting the gum tissue and underlying periosteal layer down to and along the jawbone and turning back the adjacent tissues exposing the bone over a predetermined area;

selecting a pair of spaced hollow porous cylinders of titanium wire of a height no greater than the periosteal layer spaced apart and interconnected at their bases by a strip of titanium wire mesh;

threading a temporary nylon plug into each cylinder;

assembling the cylinders and interconnected strip in overlying supported engagement with said bone surface;

applying to the interconnected cylinders and exposed bone area a strip of thin open mesh wire, portions of said open mesh strip extending laterally and longitudinally of said interconnected cylinders;

forming apertures in said open mesh strip at a center distance equal to the center distance between said cylinders, to receive said cylinders;

forming said open mesh strip to surround said cylinders;

mechanically securing adjacent cylindrical areas of said strip to, around and enclosing each of said cylinders;

reassembling the severed periosteal layer over said open mesh strip, with said cylinders embedded in said periosteal layer;

further assembling the severed gum tissue to snugly overlie said cylinders and plugs;

retaining said cylinders and plugs for a predetermined healing period of two or three months while the adjacent periosteal layer reattaches to the bone for flexibly anchoring the interconnected cylinders to said bone;

cutting the gum tissue surgically reexposing said cylinders, turning back the adjacent tissue;

unthreading and removing said plugs from said cylinders;

and successively threading into each cylinder a replacement abutment retaining device of titanium;

an axial portion thereof projecting through and from said gum tissue to which a dental or orthopedic prosthesis may be attached.

10. In the method of claim 9 the further step of reassembling the severed gum tissue into snug engagement with projecting portions of said abutment and adjacent periosteal layer.

11. In the method of claim 9, said cylinders being internally threaded;

said plugs being exteriorly threaded and having in their top surfaces a transverse screwdriver slot.

12. In the method of claim 9, said replacement abutments each including a threaded body nested into a cylinder, having a neck underlying said gum tissue and an axial shank extending from said neck through said gum tissue and terminating in an abutment head laterally enlarged relative to said neck and spaced outwardly of said gum tissue.

13. In the method of claim 9, said open mesh plastic strip being selected from the group consisting of Nylon and Teflon.

14. In the method of claim 9, said open mesh strip and the wire mesh strip between said cylinders being imbedded under the periosteal layer of said bone;

said cylinders being snugly nested within said periosteal layer, said abutments adapted to anchor and retainingly engage a prosthesis against transverse movements relative to said jawbone.

15. In the method of claim 9, the mechanical securing of said cylindrical areas of said open mesh strip to said titanium mesh cylinders including for each cylinder a snap on ring which snugly and retainingly fits over the titanium mesh cylinder and the surrounding cylindrical areas of said open mesh strip, and traps said open mesh strip thereon.

16. In the method of claim 9, said open mesh wire being of plastic.

17. In the method of claim 9, said open mesh wire being of titanium.

18. The method of implanting a pair of laterally spaced bone fastening devices upon a jawbone on opposite sides thereof for orthopedic, oral and maxillofacial surgery which comprises for each device the following steps;

locating an approximate area for implantation;

surgically cutting the gum tissue and underlying periosteal layer down to and along the jawbone and turning back the adjacent tissues exposing the bone over a predetermined area;

selecting a pair of spaced hollow porous cylinders of titanium wire mesh of a height no greater than the periosteal layer spaced apart and interconnected at their bases by a strip of titanium wire mesh;

threading a temporary nylon plug into each cylinder;

assembling the cylinders and interconnected strip in overlying supported engagement with said bone surface;

applying to the interconnected cylinders and exposed bone area a strip of thin open mesh plastic or titanium wire;

portions of said open mesh strip extending laterally and longitudinally of said interconnected cylinders;

forming apertures in said open mesh strip at a center distance equal to the center distance between said cylinders, to receive said cylinders;

forming said open mesh strip to surround said cylinders;

mechanically securing adjacent cylindrical areas of said strip to, around and enclosing each of said cylinders;

reassembling the severed periosteal layer over said open mesh strip, with said cylinders embedded in said periosteal layer;

further assembling the severed gum tissue to snugly overlie said cylinders and plugs;

retaining said cylinders and plugs for a predetermined healing period of two to three months while the adjacent periosteal layer reattaches to the bone for flexibly anchoring the interconnected cylinders to said bone;

cutting the gum tissue surgically reexposing said cylinders, turning back the adjacent tissue;

unthreading and removing said plugs from said cylinders;

and successively threading into each cylinder a replacement abutment retaining device of titanium;

an axial portion thereof projecting through and from said gum tissue to which a dental or orthopedic prosthesis may be attached.

19. A jawbone implant for orthopedic, oral and maxillofacial surgery comprising a pair of laterally spaced hollow porous cylinders of titanium wire mesh each having an internal threaded bore;

a strip of titanium wire mesh interconnecting the one ends of said cylinders;

a strip of thin open mesh plastic adapted for application to an exposed area of a jawbone from which the overlying periosteal layer and gum tissue have been surgically separated and turned back;

said cylinders and connecting strip underlying said open mesh strip;

said open mesh strip being cut to receive said cylinders;

portions of said open mesh strip being formed into cylindrical enclosures surrounding said cylinders;

and snap on rings surrounding said open mesh cylindrical formations and enclosed cylinders for securing said cylinders to said open mesh strip;

a temporary plug of nylon threaded down into each cylinder;

said cylinders and plugs adapted to be retained within said periosteal layer and overlying gum tissue for a predetermined healing period of two to three months while the adjacent periosteal layer reattaches to the bone for flexibly anchoring said cylinders and connected strip to said jawbone;

and an abutment device of titanium adapted to replace said plug within said cylinders respectively, an axial portion of each abutment projecting away from said jawbone and through said periosteal layer and gum tissue to which a dental or orthopedic prosthesis may be attached.

20. In the jawbone implant of claim 19, said replacement abutment including an elongated body having a neck underlying said gum tissue, and an axial shank extending from said neck through said gum tissue and terminating in an abutment head laterally enlarged relative to said neck spaced outwardly of said gum tissue.

21. In the jawbone implant of claim 19, each plug having a transverse screwdriver slot in its end.

22. A jawbone implant for orthopedic, oral and maxillofacial surgery comprising a pair of laterally spaced hollow porous cylinders of titanium wire mesh each having an internal threaded bore;

a strip of titanium wire mesh interconnecting the one ends of said cylinders;

a strip of thin open mesh titanium wire adapted for application to an exposed area of a jawbone from which the overlying periosteal layer and gum tissue have been surgically separated and turned back;

said cylinders and connecting strip underlying said open mesh strip;

said open mesh strip being cut to receive said cylinders;

portions of said open mesh strip being formed into cylindrical enclosures surrounding said cylinders;

and snap on rings surrounding said open mesh cylindrical formations and enclosed cylinders for securing said cylinders to said open mesh strip;

a temporary plug of nylon threaded down into each cylinder;

said cylinders and plugs adapted to be retained within said periosteal layer and overlying gum tissue for a predetermined healing period of two to three months while the adjacent periosteal layer reattaches to the bone for flexibly anchoring said cylinders and connected strip to said jawbone;

and an abutment device of titanium adapted to replace said plug within said cylinders respectively, an axial portion of each abutment projecting away from said jawbone and through said periosteal layer and gum tissue to which a dental or orthopedic prosthesis may be attached.

* * * * *